United States Patent [19]

Klauke et al.

[11] 4,161,593

[45] Jul. 17, 1979

[54] PROCESS FOR THE PREPARATION OF TRIAZINES CONTAINING A MIXTURE OF CHLORINE AND FLUORINE SUBSTITUENTS, AND OF CYANURIC FLUORIDE

[75] Inventors: Erich Klauke, Odenthal; Ernst Kysela, Bergisch-Gladbach; Alfons Dorlars, Leverkusen, all of Fed. Rep. of Germany

[73] Assignee: Bayer Aktiengesellschaft, Leverkusen, Fed. Rep. of Germany

[21] Appl. No.: 870,601

[22] Filed: Jan. 18, 1978

[30] Foreign Application Priority Data

Jan. 22, 1977 [DE] Fed. Rep. of Germany ....... 2702625

[51] Int. Cl.$^2$ ............................................. C07D 251/28
[52] U.S. Cl. ................................................. 544/217
[58] Field of Search ......................................... 544/217

[56] References Cited

U.S. PATENT DOCUMENTS

| 2,845,421 | 7/1958 | Grundmann et al. ............... 544/217 |
| 3,162,632 | 12/1964 | Olstowski ............................ 544/217 |

FOREIGN PATENT DOCUMENTS

| 630984 | 11/1961 | Canada .................................... 544/217 |
| 599625 | 6/1970 | Canada .................................... 544/217 |
| 1044091 | 11/1958 | Fed. Rep. of Germany .......... 544/217 |
| 873251 | 7/1961 | United Kingdom .................... 544/217 |

OTHER PUBLICATIONS

Grisley et al., J. Org. Chemistry, vol. 23, pp. 1802–1804 (1958).
Kwasnik, FIAT Review of German Science, 1939–1946, Klemm "Inorganic Chemistry," Part I, p. 243, pub. 1948, Ed. Walter Rudorff.
Maxwell et al., J. Amer. Chem. Soc., vol. 80, pp. 548–549 (1958).
Kober et al., J. Org. Chem., vol. 27, pp. 2577–2580 (1962).

*Primary Examiner*—John M. Ford
*Attorney, Agent, or Firm*—Plumley and Tyner

[57] ABSTRACT

Process for the preparation of triazines containing a mixture of chlorine and fluorine substituents, characterized in that cyanuric chloride is heated with cyanuric fluoride to temperatures from 30°–300° C. in the presence of suitable catalysts.

5 Claims, No Drawings

PROCESS FOR THE PREPARATION OF TRIAZINES CONTAINING A MIXTURE OF CHLORINE AND FLUORINE SUBSTITUENTS, AND OF CYANURIC FLUORIDE

The present invention relates to a process for the preparation of triazines containing a mixture of chlorine and fluorine substituents, characterised in that cyanuric chloride is heated with cyanuric fluoride to temperatures from 30°–300° C., in particular 60°–180° C. and preferably 80°–150° C., in the presence of suitable catalysts.

The ratio of cyanuric chloride:cyanuric fluoride can be varied within wide limits, for example from 1:10 to 10:1. Furthermore, the composition of the reaction product obtained can be varied within wide ranges by suitably choosing the temperature and time.

Suitable catalysts are, for example, antimony-V compounds, in particular the corresponding halides, such as $SbF_5$ and $SbCl_5$, and also aluminium halides, titanium halides, tin halides and iron halides, such as $AlCl_3$, $TiCl_4$, $SnCl_4$ and $FeCl_3$, as well as, in particular, active charcoal. In general, the catalysts are employed in amounts of 0.1–5% by weight, preferably 0.5–1.5% by weight.

It has also been found that it is advantageous to use HCl as a promoter for the catalysts. The use of HCl accelerates the disproportionation.

In general, the reaction is carried out by heating the components in an autoclave under a nitrogen atmosphere or under a partial pressure of HCl. After the reaction has ended, the reaction mixture is worked up in the customary manner by distillation.

The reaction products, that is to say difluoro-chloro-triazine and dichloro-fluoro-triazine can be isolated in the pure form by distillation. Like the starting materials, they are known compounds and can be used, for example, as intermediate products for herbicidal active compounds or reactive dyestuffs.

The process for the disproportionation of cyanuric chloride/cyanuric fluoride can also be applied to other perhalogenated N-heterocyclic compounds. For example, if 50 g of 2,4,6-trifluoro-5-chloropyrimidine and 50 g of tetrachloropyrimidine are heated to 250° C. with 1 g of active charcoal for 2 hours, a mixture is obtained which, according to gas chromatography, has the following composition: 31.6% of 2,4,6-trifluorochloropyrimidine, 15.0% of difluorodichloropyrimidine, 17.1% of fluorotrichloropyrimidine and 34.0% of tetrachloropyrimidine, or, for example, when 40 g of tetrafluoropyridazine and 40 g of tetrachloropyridazine are allowed to react with 0.8 g of A-charcoal for 3 hours at 150° C., a reaction product is obtained which, according to gas chromatography, has the composition: 35.9% of tetrafluoropyridazine, 11.8% of trifluorochloropyridazine, 5.3% of difluorodichloropyridazine, 17.4% of fluorotrichloropyridazine and 29.0% of tetrachloropyridazine.

The mixtures contained by heating cyanuric chloride with cyanuric fluoride in the presence of catalysts are also preferably used for the preparation of cyanuric fluoride.

The present invention thus furthermore relates to a process for the preparation of cyanuric fluoride, which is characterised in that a mixture of cyanuric chloride and cyanuric fluoride, preferably in the molar ratio of about 6:1–1:1, preferably 4:1–2:1, is first heated to 30°–300° C., in particular 60°–180° C. and preferably to 80°–150° C., in the presence of catalysts, in particular the abovementioned catalysts, in general for about 0.2 to 2 hours, and the reaction mixture is then reacted with anhydrous HF at temperatures from about −20° C. to +70° C. In this procedure, an excess of HF is preferably used, for example up to 5 mols per equivalent of chlorine to be replaced.

Under conditions of normal pressure, the fluorination reaction proceeds sufficiently rapidly and completely in the range from −10° C. to room temperature. However, as already indicated above, good cooling is necessary to separate off the HF carried, in proportion to the vapour pressure, with the escaping hydrogen chloride. Both the HF and the low-boiling reaction product should be led into the reaction vessel again by reflux. This can be made considerably easier still technically, by carrying out the reaction under a slight excess pressure up to about 6 bars. The boiling point of HF and cyanuric fluoride is thereby increased and the off-gas purification made easier.

In order to accelerate the Cl/F exchange towards the end of the reaction, it can be appropriate also to increase the temperature briefly. For this it is sufficient to increase the temperature up to 30°–40° C. when the evolution of HCl subsides and to allow the reaction to go to completion at this temperature. The HCl still liberated during this procedure is let down via a regulating valve under a pressure of 3–6 atmospheres gauge. After the fluorination reaction has ended, the reaction mixture is worked up in the customary manner by distillation.

EXAMPLE 1

120 g of cyanuric chloride, 100 g of cyanuric fluoride and 6.6 g of $SbF_5$ are introduced into an autoclave. A protective pressure of about 2 bars of nitrogen is then applied and the mixture is heated to 120° C. and stirred for 3 hours at this temperature. It is then cooled and the pressure is let down. According to the gas chromatogram, the residue has the following composition:

| Cyanuric fluoride | Difluorochloro-triazine | Dichlorofluoro-triazine | Cyanuric chloride |
|---|---|---|---|
| 23.5% | 19.4% | 30.7% | 20.0% |

EXAMPLE 2

120 g of cyanuric chloride and 100 g of cyanuric fluoride are stirred with 12 g of A-charcoal for 3 hours at 120° C. in an autoclave. According to the gas chromatogram, the reaction mixture has the following composition:

| Cyanuric fluoride | Difluorochloro-triazine | Dichlorofluoro-triazine | Cyanuric chloride |
|---|---|---|---|
| 16.3% | 39.9% | 38.5% | 4.9% |

The pure components are isolated by fractional distillation:

| | | | |
|---|---|---|---|
| cyanuric fluoride | boiling point$_{760}$ | 73° | $n_D^{20}$: 1.3842 |
| 1,3-difluoro-5-chloro-triazine | boiling point$_{760}$ | 113° | $n_D^{20}$: 1.4493 |
| 1-fluoro-3,5-dichloro- | | | |

| | | | |
|---|---|---|---|
| triazine | boiling point_{760} 154° | $n_D^{20}$: | 1.5060 |

EXAMPLE 3

If 200 g of cyanuric chloride and 100 g of cyanuric fluoride are allowed to react with 3 g of active charcoal for 2 hours at 180° C., a reaction product of the following composition is obtained

| | Cyanuric fluoride % | Difluoro-chloro-triazine % | Dichloro-fluoro-triazine % | Cyanuric chloride % |
|---|---|---|---|---|
| | 5.9 | 26.3 | 42.6 | 24.8 |
| with 1.5 g of A-charcoal | 13.2 | 14.7 | 21.9 | 46.7 |
| with 0.3 g of A-charcoal | 24.4 | 6.5 | 7.2 | 61.5 |

At the same temperature and a reaction time of only 30 minutes, the composition is (3 g of active charcoal)

| Cyanuric fluoride | Difluorochloro-triazine | Dichlorofluoro-triazine | Cyanuric chloride |
|---|---|---|---|
| 8.4% | 20.3% | 33.9% | 36.1% |

If cyanuric chloride and cyanuric fluoride are employed in the molar ratio of 1:1 under these reaction conditions of 30 minutes/180° C., the composition of the reaction product is then

| Cyanuric fluoride | Difluorochloro-triazine | Dichlorofluoro-triazine | Cyanuric chloride |
|---|---|---|---|
| 12.7% | 32.0% | 35.6% | 19.0% |

EXAMPLE 4

In each case 92.5 g of cyanuric chloride (A) and 67.5 g of cyanuric fluoride (B) are introduced into an autoclave with 1.6 g of catalyst, the mixture is heated rapidly to the reaction temperature under a protective pressure of 5 bars of $N_2$, kept at this temperature for 30 minutes and cooled, the pressure is let down and the composition is determined by gas chromatography. The table gives the values for different catalysts: (C=difluorochlorotriazine; D=dichlorofluorotriazine)

| | Catalyst | Temperature | B | C | D | A |
|---|---|---|---|---|---|---|
| (1.) | SbCl_5 | 180° C. | 34.2% | 8.2% | 17.0% | 40.4% |
| (2.) | SbF_5 | 180° C. | 30.6% | 11.7% | 25.1% | 32.4% |
| (3.) | FeCl_3 | 180° C. | 31.2% | 10.3% | 23.6% | 34.8% |
| (4.) | AlCl_3 | 250° C. | 32.0% | 12.7% | 18.4% | 36.6% |
| (5.) | SnCl_4 | 250° C. | 33.1% | 11.5% | 24.3% | 28.6% |
| (6.) | TiCl_4 | 250° C. | 23.8% | 13.2% | 28.5% | 29.4% |

If experiment (1) is repeated with the difference that before the nitrogen protective pressure is applied a pressure of 0.5 bar of HCl is applied, the values according to gas chromatography are then

| B | C | D | A |
|---|---|---|---|
| 20.2 | 16.2 | 34.4 | 29.0 |

EXAMPLE 5

The following series of experiments demonstrate the temperature dependence of the disproportionation.

Equal amounts by weight of cyanuric chloride and cyanuric fluoride are allowed to react in the presence of 3% of active charcoal for 3 hours. The table shows the composition, according to gas chromatography, at different temperatures.

| Temperature | B | C | D | A |
|---|---|---|---|---|
| 120° | 18.5 | 39.3 | 31.3 | 10.7 |
| 100° | 31.9 | 25.6 | 19.0 | 23.4 |
| 80° | 43.7 | 12.8 | 9.5 | 33.8 |
| 60° | 55.5 | 1.6 | 0.3 | 44.4 |

EXAMPLE 6

800 g of cyanuric chloride and 200 g of cyanuric fluoride are introduced into an autoclave with 5 g of active charcoal. After applying a protective pressure of about 2 bars of $N_2$, the mixture is heated up to 180° C. and stirred for 30 minutes at this temperature. It is then cooled, the pressure is let down and a reflux condenser with a regulating valve is mounted on the autoclave. 650 ml of HF are allowed to run in at an internal temperature of about 10° C., whilst stirring vigorously. After the addition has ended, the autoclave is closed and the regulating valve is set at a pressure of 3 bars. The mixture is then heated to 30° C. and the reaction is allowed to proceed between 30°–55° C. After about 4 hours, the evolution of HCl has subsided. The autoclave is cooled, let down and refitted for distillation. The excess HF is first distilled off (210 ml). 540 g of cyanuric fluoride of boiling point: 72°–4° C. are then distilled off.

The residue remains in the kettle and is re-employed in the next batch as cyanuric fluoride for the disproportionation reaction.

We claim:

1. Process for the preparation of triazines containing a mixture of chlorine and fluorine substituents, characterised in that cyanuric chloride is heated with cyanuric fluoride to temperatures from 30°–300° C. in the presence of suitable catalysts.

2. Process according to claim 1, characterised in that the mixture is heated to temperatures from 60°–180° C., preferably 60°–150° C.

3. Process according to claim 1, characterised in that cyanuric chloride and cyanuric fluoride are reacted in the molar ratio of 1:10 to 10:1.

4. Process according to claim 1, characterised in that active charcoal and antimony-V halides, aluminium halides, titanium halides, tin halides and iron halides are used as the catalysts.

5. Process according to claim 4, characterised in that the catalysts are employed in amounts from 0.1–5% by weight, preferably 0.5–1.5% by weight.

* * * * *